United States Patent
Kroll et al.

[11] Patent Number: 5,871,510
[45] Date of Patent: Feb. 16, 1999

[54] METHOD AND APPARATUS FOR TEMPORARILY ELECTRICALLY FORCING CARDIAC OUTPUT AS A BACKUP FOR TACHYCARDIA PATIENTS

[76] Inventors: Kai Kroll, 5217 W. Mill Rd., Minnetonka, Minn. 55345; Mark W. Kroll, 13011 Brenwood Trail, Minnetonka, Minn. 55343

[21] Appl. No.: 548,234

[22] Filed: Oct. 25, 1995

Related U.S. Application Data

[63] Continuation-in-part of Ser. No. 251,349, May 31, 1994, abandoned, and a continuation of Ser. No. 543,001, Oct. 13, 1995, abandoned, and Ser. No. 754,712, Dec. 6, 1996.

[51] Int. Cl.[6] .................................................. A61N 1/362
[52] U.S. Cl. ............................................................. 607/14
[58] Field of Search ....................................... 607/4, 5, 14

[56] References Cited

U.S. PATENT DOCUMENTS

| | | |
|---|---|---|
| 3,638,656 | 2/1972 | Grandjean et al. . |
| 4,181,133 | 1/1980 | Kolenick et al. . |
| 4,222,386 | 9/1980 | Smolnikov et al. . |
| 4,280,502 | 7/1981 | Baker et al. . |
| 4,349,030 | 9/1982 | Belgard et al. . |
| 4,390,021 | 6/1983 | Spurrell et al. . |
| 4,398,536 | 8/1983 | Nappholz et al. . |
| 4,408,606 | 10/1983 | Spurrell et al. . |
| 4,488,553 | 12/1984 | Nappholz et al. . |
| 4,488,554 | 12/1984 | Nappholz et al. . |
| 4,830,006 | 5/1989 | Haluska et al. . |
| 4,945,909 | 8/1990 | Fearnot et al. . |
| 4,996,984 | 3/1991 | Sweeney et al. . |
| 5,018,522 | 5/1991 | Mehra et al. . |
| 5,042,497 | 8/1991 | Shapland et al. . |
| 5,330,509 | 7/1994 | Kroll et al. . |
| 5,336,245 | 8/1994 | Adams et al. . |

FOREIGN PATENT DOCUMENTS

| | | |
|---|---|---|
| 540266 | 5/1993 | European Pat. Off. . |
| 9306886 | 4/1993 | WIPO . |
| 9319809 | 10/1993 | WIPO . |

OTHER PUBLICATIONS

Kirchhof, et al.* "Regional Entrainment of Atrial Fibrillation Studied by High Resolution Mapping in Open–Chest Dogs" Circulation 1993; 88: 736–749.

Ken Knight, et al.* "Regional Capture of Fibrillating Right Ventricular Myocardium: Evidence of an Excitable Gap in VF Using High Resolution Cardiac Mapping." J. Am Coll Card 1994: 283 A.

Schuder, et al.* "Transthoracic Ventricular Defibrillation in Dogs With Unidirectional Rectangular Double Pulses." Cardiovasc Res. 1970; 4: 497–501.

Kugelberg, et al.* "Ventricular Defibrillation with Double Square Pulses." Med & Biol Eng., 1968; 6: 167–169.

Kugelberg, et al.* "Ventricular Defibrillation: A New Aspect." Acta Chirurgica Scandinavia 1967: Supplement 372.

Resnekov* "Ventricular Defibrillation by Monophare Trapezoidal shaped Double–pulses of Low Electrical Energy." Cardiovasc Res. 1968; 2: 261–264.

Geddes, et al.* "Ventricular Defibrillation with Single and Twin Pulses of Half–Sinusoidal Current." J Applied Physiology, 1973; 34: 8–11.

Primary Examiner—William E. Kamm
Attorney, Agent, or Firm—Patterson & Keough, P.A.

[57] ABSTRACT

A novel backup approach for tachycardia patients is taught. This approach uses the application of electrical cardiac output forcing to maintain a partial cardiac contraction in the event that antitachycardia therapy accelerates the patients' rhythm into a fibrillation. The partial contraction forces cardiac output at a level sufficient to maintain life.

23 Claims, 15 Drawing Sheets

HIGH COMFORT PULSE

HIGH EFFICIENCY PULSE

METHOD AND APPARATUS FOR TEMPORARILY ELECTRICALLY FORCING CARDIAC OUTPUT AS A BACKUP FOR TACHYCARDIA PATIENTS

This application is a continuation-in-part of Ser. No. 08/251,349, filed on May 31, 1994, entitled, "Method and Apparatus for Temporarily Electrically Forcing Cardiac Output in a Tachyrhythmia Patient" which application is now abandoned and was continued under FWC Ser. No. 08/543,001, filed on Oct. 13, 1995, which application was also abandoned in favor of FWC Ser. No. 08/754,712, filed on Dec. 6, 1996, which is currently pending.

FIELD OF THE INVENTION

The invention generally relates to a method and device for therapies in the treatment of cardiac arrythmias. Specifically, the present invention provides method and apparatus for temporarily forcing cardiac output in the event of fibrillation resulting from an unsuccessful antitachycardia pacing therapy.

BACKGROUND OF THE INVENTION

Many patients suffer from an occasional condition of ventricular tachycardia (VT). This is particularly prevalent in patients who survive heart attacks. Generally, VT is an on-set of a condition in which the bottom chambers of the heart (ventricles) beat at a high rate. In sharp contrast to Ventricular fibrillation (VF), VT is not usually life-threatening. However, there are situation in which VT could be fatal. Generally, VT may cause fainting, loss of consciousness, anxiety and may occasionally degenerate into a fatal VF. Accordingly, while VT is not as serious as VF, it is nonetheless a condition that calls for prompt therapy and treatment.

Prior art therapy methods and devices utilize low voltage timed pulses to control VT. Some of the prior art references which teach antitachycardia pacing using low voltage shock therapy systems include U.S. Pat. No. 4,408,606, U.S. Pat. No. 4,398,536, U.S. Pat. No. 4,488,553, U.S. Pat. No. 4, 488,554, and U.S. Pat. No. 4,390,021, all assigned to Telectronics. Other patents dealing with antitachycardia pacing (ATP) include U.S. Pat. No. 4,181,133 and U.S. Pat. No. 4,280,502, assigned to Intermedics.

Generally, a limitation of the prior art is the fact that low voltage shock therapy for use in antitachycardia pacing may accelerate the VT and may transform it into a lethal VF. In an attempt to reduce this risk, it was necessary to equip patients with a separate implantable defibrillator in the event an antitachycardia pacing therapy for VT induces a VF. However, this arrangement was not only expensive but also rather bulky and inconvenient for the patient. An alternate solution has been to equip an implantable cardioverter defibrillator (ICD) with an antitachycardia pacing device. Such a configuration is disclosed in U.S. Pat. No. 4,830,006.

In spite of the many advances made by the prior art, most of the configurations and devices are cumbersome, expensive and inconvenient for the patient. Specifically, most of the devices incorporated with an ICD require a space-volume of between 60 to 100 Cubic centimeters in volume partly because of the need for large batteries and capacitors.

Accordingly, there is need for a compact antitachycardia pacemaker which is both practicable and space-volume efficient to be implanted in patients to provide specific therapy for VT.

SUMMARY OF THE INVENTION

The present invention provides a method and device for antitachycardia pacing therapy. Specifically, the method includes stimulating fibrillating cardiac cells using a predetermined level of voltage pulses at a specified rate and duration to induce a partial contraction of the heart. This approach is advantageously implemented as a backup for antitachycardia pacing in the event that an ATP transforms a VT into a VF.

Specifically, the present invention utilizes a unique method and device to implement electrical cardiac output forcing (ECOF) at a level sufficient to maintain the life and consciousness of the patient until emergency care and external defibrillation could be performed. To this end, the present invention provides a compact and energy efficient system which can be used as a backup for antitachycardia pacing.

DETAILED DESCRIPTION OF THE PREFERRED EMBODIMENTS

The present invention will now be described more fully hereinafter with reference to the accompanying drawings, in which preferred embodiment of the invention are shown. This invention may, however, be embodied in many different forms and should not be construed as limited to the embodiment set forth herein. Rather, applicants provide these embodiments so that this disclosure will be thorough and complete, and will convey the scope of the invention to those skilled in the art.

Figure 1:
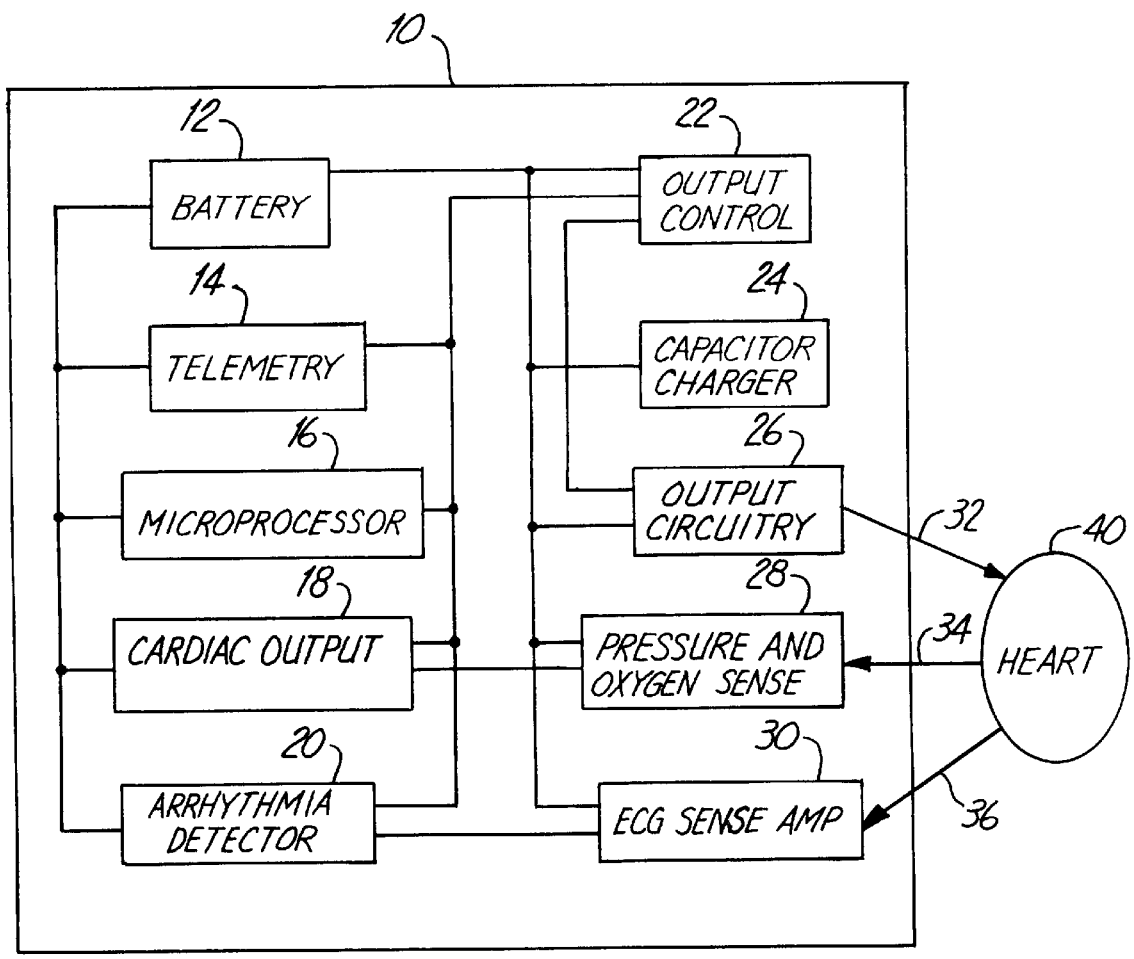
FIG. 1 is a block diagram illustrating a system constructed in accordance with the principles of the present invention.

FIG. 1 is a block diagram illustrating a system 10 constructed in accordance with the principles of the present invention. The device circuitry is connected to the heart 40 via a series of leads; output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; fibrillation, tachycardia or asystole. The circuit also contains an optional pressure sensing section 28 which amplifies and conditions a signal from an optional pressure sensor from within the heart or artery. The output of the pressure sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if Electrical Cardiac Output Forcing (ECOF) is appropriate. If forcing is indicated, the microprocessor 16 prompts the output control 22 to charge a capacitor within the output circuit 26 via the capacitor charger 24. The output control 22 directs the output circuitry 26 to deliver the pulses to the heart 40 via the output leads 32. The microprocessor 16 may communicate with external sources via a telemetry circuit 14 within the device 10. The power for the device 10 is supplied by an internal battery 12.

Figure 2:
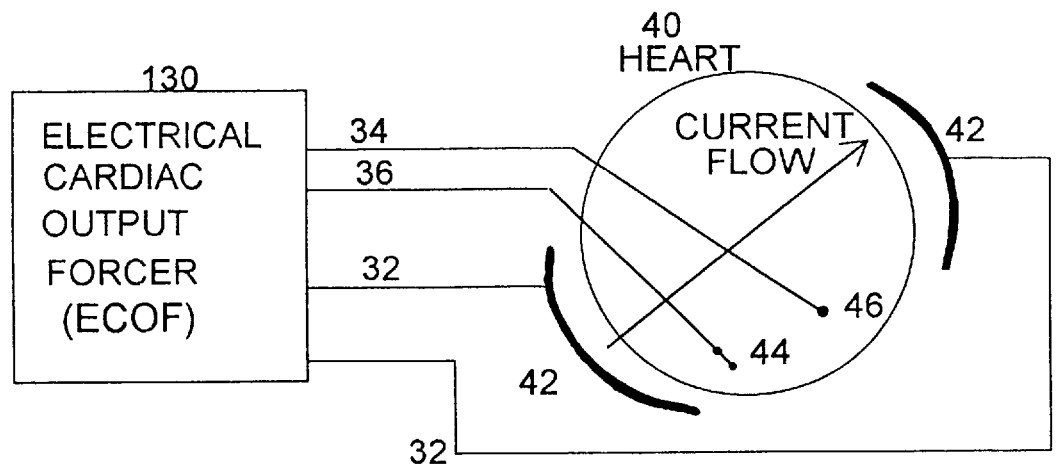
FIG. 2 shows a connection of an implantable embodiment of the device to the heart in an epicardial patch configuration.

FIG. 2 is a diagram showing the connection of the device 130 to the heart 40 in an epicardial patch configuration. In this configuration, current passes through an output lead pair 32 to electrode patches 42 which direct the current through the heart 40. There is an optional pressure sense lead 34 which passes the signal from an optional pressure transducer 46 which lies in the heart 40. The ECG is monitored by sense electrodes 44 and passed to the device 130 by a lead 36. The area of the electrodes 42 is a least 0.5 cm2. The size of the electrode is greater than that of a pacing lead and no more than that of a defibrillation electrode or between approximately 0.5 cm2 and 20 cm2 each.

Figure 3:
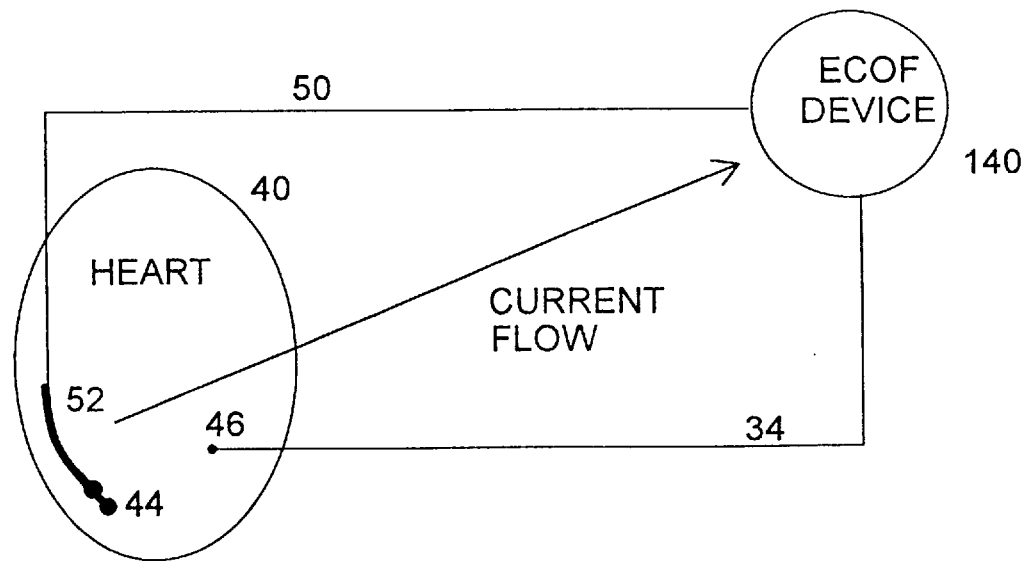
FIG. 3 shows the connection of an implantable embodiment of the device to the heart using an endocardial lead system and the device housing as an electrode.

FIG. 3 shows a non-thoractomy system embodiment of the invention. In this system, the current passes from a coil electrode 52 in the heart 40 to the housing of the device 140. An endocardial lead 50 combines the ECG sensing lead and the pulse output lead. The ECG is monitored by sense electrodes 44 in the heart 40 and passes through the endocardial lead 50. There is an optional pressure transducer 46 in the heart 40 which passes a signal to the device 140 via optional lead 34.

Figure 4:
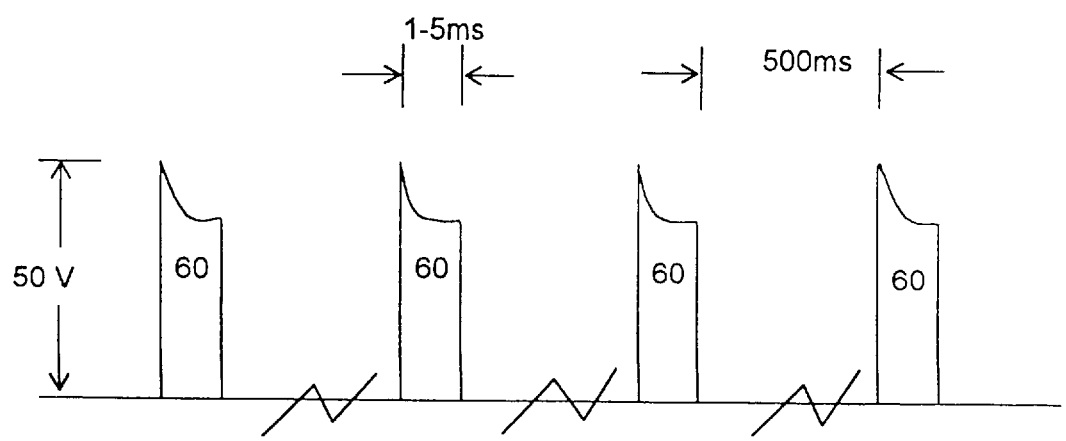
FIG. 4 is a diagram showing a representative pulsatile electrical signal.

A series of forcing pulses 60 are shown in FIG. 4. The pulses are approximately 50 V in amplitude with a spacing of approximately 500 ms. The 50 V and the 500 ms pulse spacing are chosen as illustrative for an implantable embodiment. The forcing pulse interval is chosen to maximize cardiac output within the limits of the device circuitry and the response of the heart muscle. An interval of 500 ms corresponds to a heart rate of 120 beats per minute. This will produce a greater output than a typical resting rate of 60 beats per minute. However, a rate of 240 beats per minute would produce a lower output due to mechanical limitations of the heart. Thus a practical range is 60 to 200 beats per minute is appropriate. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50Ω, the power during the pulse is $P=V^2/R=50\ V*50\ V/50\Omega=50\ W$. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes. (10,000 J/4.8 W=2083 seconds). Thirty five minutes may not be enough time to transport the patient to a hospital. Therefore 200 V represents the highest practical voltage for continuous operation in an implantable embodiment, although voltages of up to 350 V (maximum voltage for electrolytic capacitors) could be used for short periods and adjusted down when hemodynamic output is verified. A practical lower limit is about 10 V. During normal sinus rhythm, 10 V delivered through the patches would pace. However, during fibrillation the 10 V could not pace and only cells very near the electrodes would be captured. This would be insufficient for forcing cardiac output. A typical range would be 30–200 V with an optional 350 V initial burst.

These calculations also suggest other differences between an implantable ECOF and an ICD. With a battery storing 10,000 J and an ECOF pulse having 0.1 J, this ECOF would be capable of delivering 100,000 pulses. An ICD can only deliver 200–400 shocks of about 30 J. The ECOF is also very different from an implantable pacemaker which typically delivers 150,000,000 pacing pulses (5 years at 60 BPM) each of about 0.00005 J.

Figure 5:
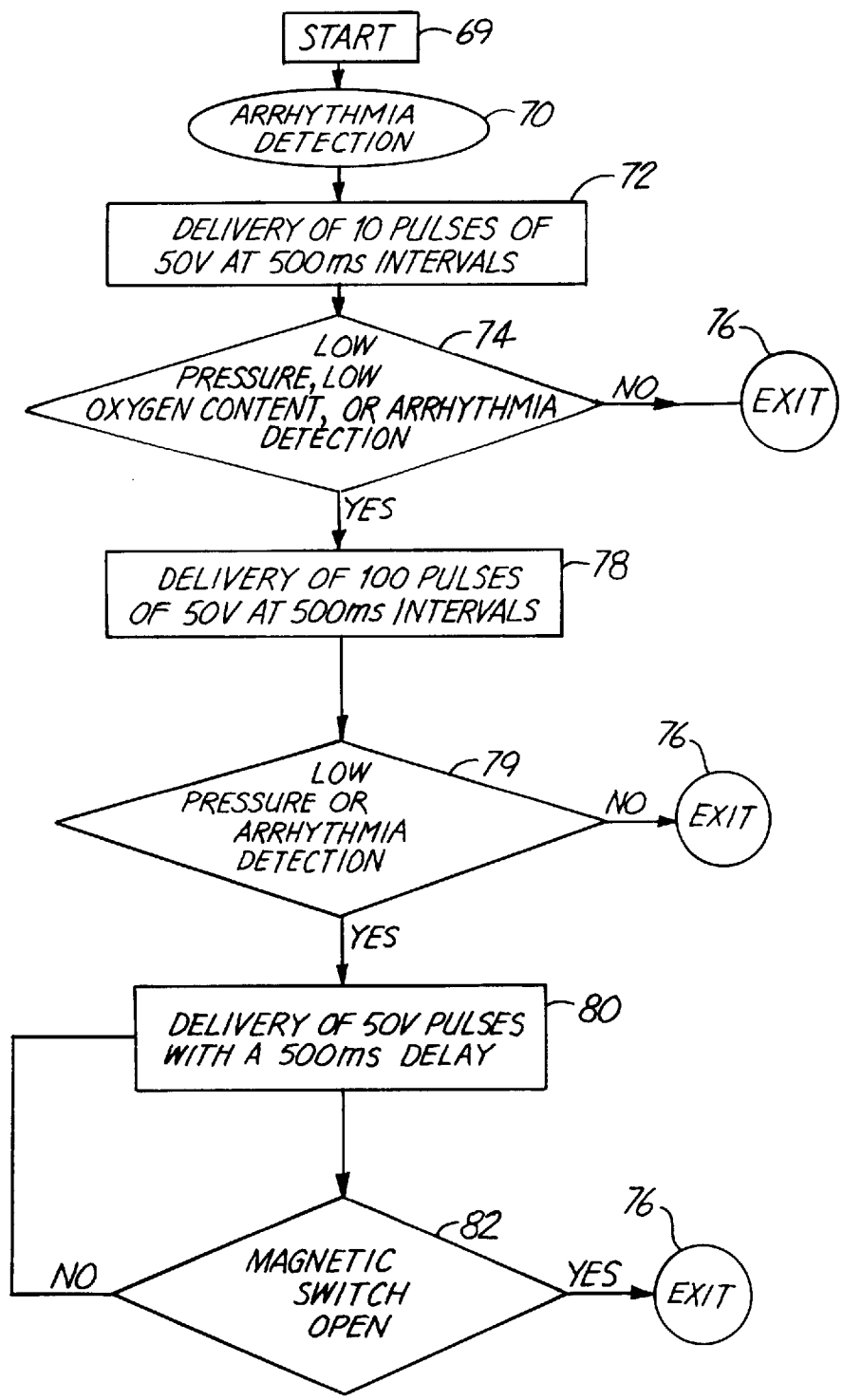
FIG. 5 is a flowchart illustrating one embodiment of the method of the invention.

FIG. 5 is a flowchart illustrating the method of the invention, which is provided for purposes of illustration only. One skilled in the art will recognize from the discussion that alternative embodiments may be employed without departing from the principles of the invention. The flow diagram shown in FIG. 5 represents a method of automatically treating a heart which is in fibrillation, tachycardia, or asystole and thereby pumping inefficiently or not at all. Electrodes are attached 69. A diagnosis of the presence of an arrhythmia is made 70. A series of cardiac output forcing electric pulses 72 is automatically delivered. It should be understood that the therapy 72 may be delivered for any output compromising cardiac arrhythmia. After delivery of 10 forcing pulses (at a rate of 60–200 BPM) in the first block 72, the status of the heart is determined 74. If an arrhythmia is still present and there exists low pressure within the heart, more forcing pulses are delivered 78. If the heart is pumping at a safe level, the therapy ceases and exits 76. Note that this means that the ECOF successfully defibrillated the patient's heart even though this is not a primary goal of the system. This could be tested in patients who were scheduled to receive an ICD, in a hospital setting. Those patients who are defibrillated by ECOF pulse therapy could then receive the ECOF instead of the larger ICD. After the therapy 78 has been delivered, the pressure and ECG is again monitored 74. If the therapy 78 is successful, it ceases and exits 76. If the therapy 78 is unsuccessful in producing a safe level of pumping efficiency, the method proceeds to a continuous cardiac assist mode 80. The therapy may only be stopped by an external command, for example, a telemetry signal or a magnet which is applied to the chest activating a magnetic reed switch 82 which terminates the therapy and exits 76. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 6:
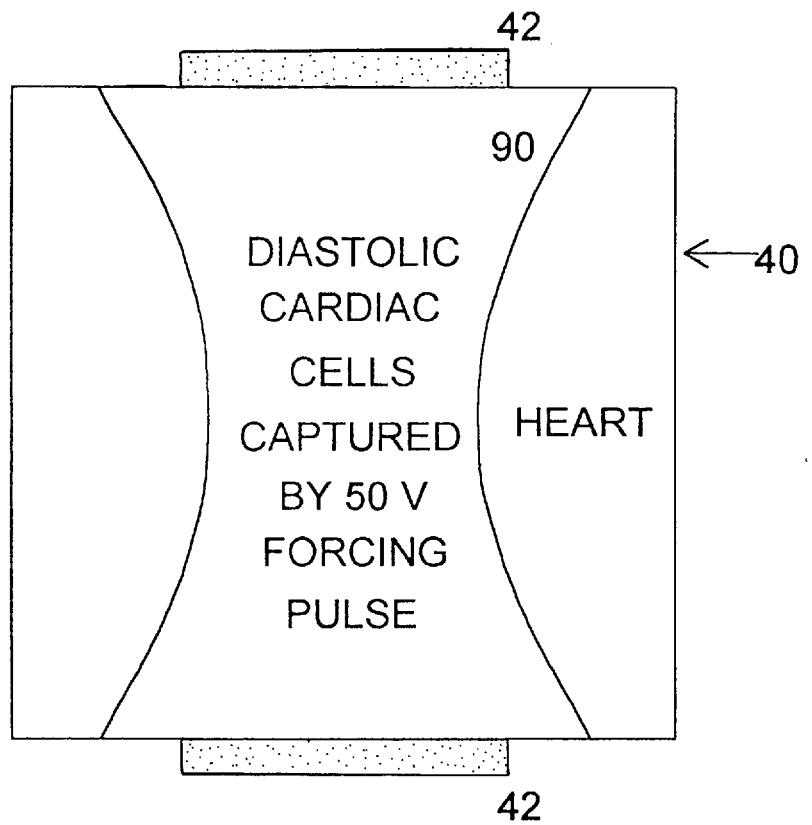
FIG. 6 is a diagram showing the expected effect of a 50 V pulse on the heart during diastole.

FIG. 6 is a diagram showing the effect of a 50 V forcing pulse on the heart 40 during electrical diastole (cells at rest). The current is passed through the heart 40 by the electrodes 42. Approximately 60% of cardiac cells 90 would be captured by a 50 V pulse if the cells were in diastole. The captured cells 90 mostly lie in the direct path between the electrodes 42 and near the electrodes 42 where the field strengths are highest. Of course, over a time period of about 100 ms these directly captured cells then propagate an activation wavefront to stimulate the rest of the heart. This so called far-field pacing is irrelevant here as the hearts, of interest, are in fibrillation and not in diastole.

Figure 7:
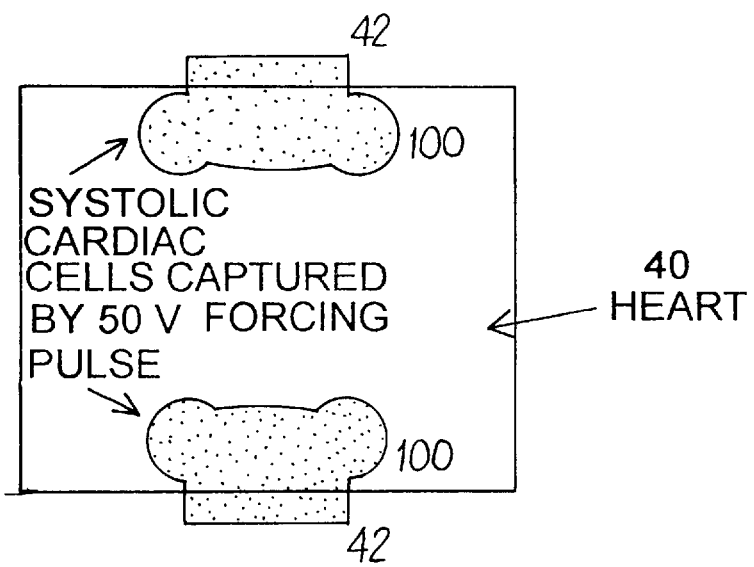
FIG. 7 is a diagram showing the expected effect of a 50 V pulse on the heart during systole.

FIG. 7 is a diagram showing the effect of a 50 V forcing pulse on the heart during electrical systole (cells already stimulated). The current is passed through the heart 40 by the electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (5 V/cm) than those required for diastolic cell capture (0.5 V/cm).

Figure 8:
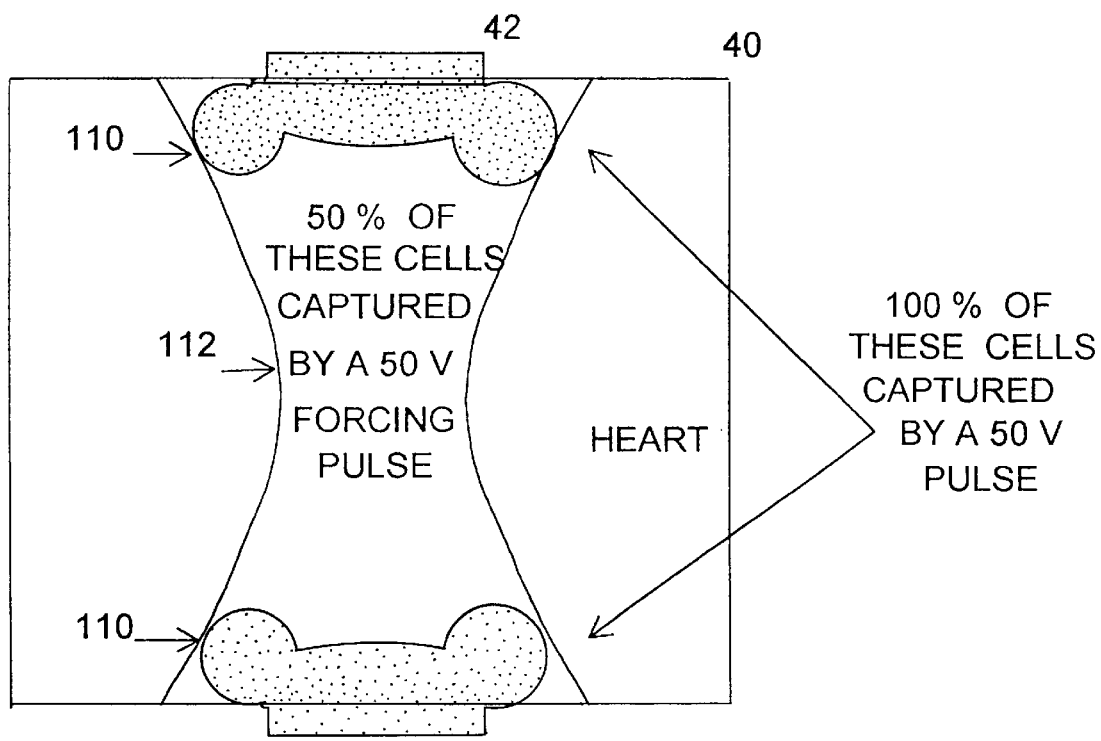
FIG. 8 is a diagram showing the expected effect of a 50 V pulse on the heart during fibrillation.

FIG. 8 is a diagram showing the effect of a 50 V forcing pulse on the heart during fibrillation. During fibrillation there are always cells in systole and diastole simultaneously. But, the vast majority are in systole. The diagram assumes 50% of the cells are in diastole which applies only after several capturing pulses. The current is passed through the heart 40 by the electrodes 42. 100% of the cells 110 nearest the electrodes 42 would be captured due to the high field strength. As shown in FIG. 7, even systolic cells are captured by high field strengths. 50% of the cells 112 in the direct path between the electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the resulting mechanical action and the contribution to cardiac output forcing.

Considering the cardiac cells that are originally in diastole, (rows A&B in the table below), the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next consider the activity of the systolic cells (rows C&D). If 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result (Rows A, B, C, and D) is a gain in contraction which forces cardiac output.

| Original Status of the Cells | Percentage of the Cardiac Cells | Status of the Cardiac Cells | Percentage of the Original Status | Percentage of the Total Cells | Mechanical Action | Forcing Cardiac Output Effect |
|---|---|---|---|---|---|---|
| (A) Diastolic | 50% | Diastolic non-captured | 40% of 50% | 20% | will start to contract on own | positive (+) |
| (B) Diastolic | | Diastolic captured | 60% of 50% | 30% | contract | positive (++) |
| (C) Systolic | 50% | Systolic non-captured | 80% of 50% | 40% | will start to relax on own | negative (−) |
| (D) Systolic | | Systolic captured | 20% of 50% | 10% | hold | neutral (0) |
| TOTAL | 100% | | 100% | 100% | more contraction | positive (+) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field |
| C | Systolic non-captured | −5% | Negative. Some cells will begin to relax on their own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4–5 times reserve capacity.

Figure 9:
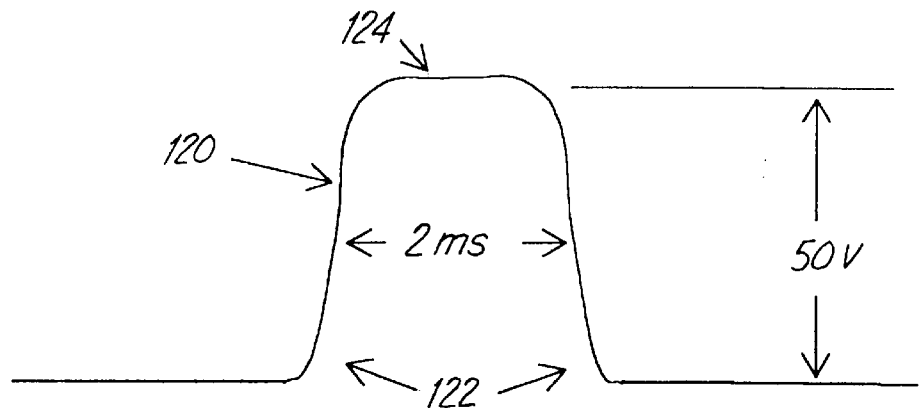
FIG. 9 shows a high comfort rounded pulse.

FIG. 9 depicts an example of a waveform designed to minimize the twitching of the chest muscles which can be very uncomfortable to the patient. A low harmonic pulse waveform 120 has a very gradual "foot" 122 and a gradual peak 124. Such a pulse has less high frequency energy components and thus is less likely to stimulate the skeletal muscle.

Figure 10:
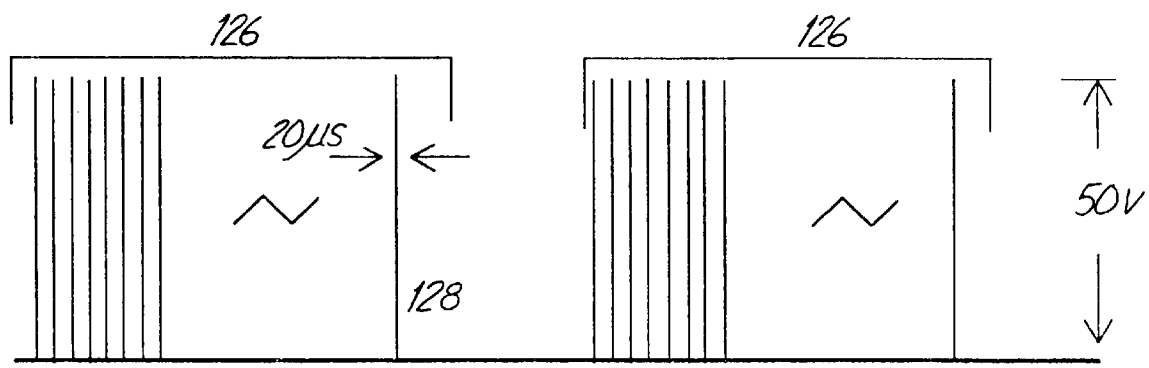
FIG. 10 shows a pulse comprised of many smaller pulses.

FIG. 10 shows a technique of going to the opposite extreme. Here, each compound forcing pulse 126 is actually composed of 50 very short spikes 128 each of which is 20 μs in width with a 20 μs spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to charge the capacitor to 300 V for the first pulse to capture many cells therefore putting those cells into diastole after a delay of 100–200 ms. At this point the voltage could be lowered to 100 V and pulses delivered every 100 ms. A 3 watt DC-DC converter with a 67% efficiency could provide 100 ms interval forcing pulses assuming a 50Ω resistance and 1 ms pulse (0.2 J). This rate is too fast for forcing cardiac output due to mechanical limitations, but is very effective for electrical capture. After sufficient capture, the rate of forcing pulses could be slowed down to 100–170 beats per minute for optimum cardiac output.

Figure 11:
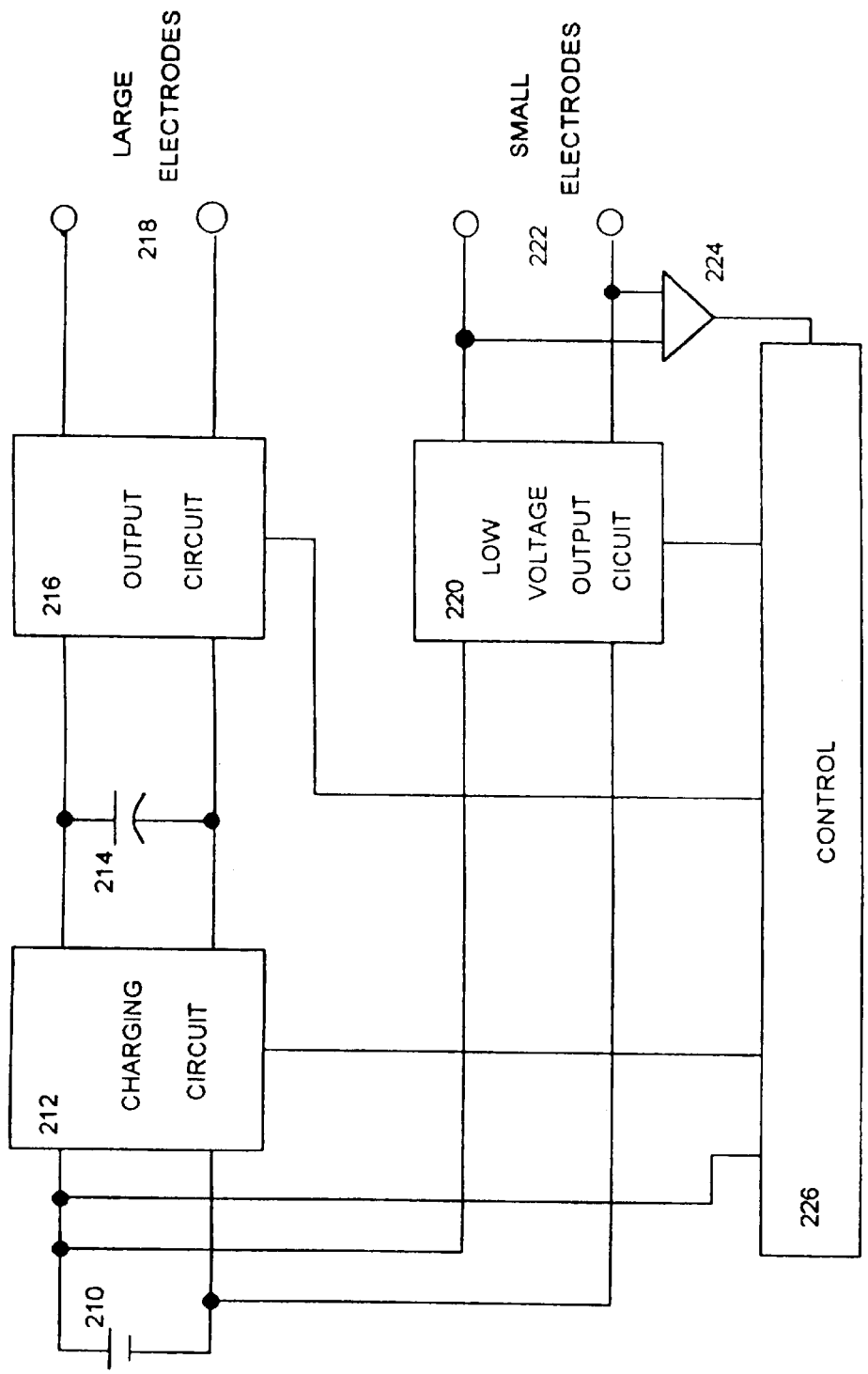
FIG. 11 is a block diagram illustrating a system constructed in accordance with the principles of the present invention.

FIG. 11 is a block diagram of one embodiment of the invention. Battery 210 is used to provide power for all circuitry in this embodiment. This includes the charging circuit 212 which provides the means to charge up capacitor 214 in the event that ECOF (electrical cardiac output forcing) is required. The output circuit 216 is then used to deliver the electrical current pulses from the energy stored in capacitor 214 to the large cardiac electrodes 218.

The battery 210 also provides the power to the low voltage output circuit 220 which in turn provides pacing pulses to the small cardiac electrodes 222. These small cardiac electrodes are also used to sense the cardiac activity which is then run through amplifier 224 and thence delivered to the control unit 226. This control unit is also responsible for controlling the charging circuit 212 and both the higher output voltage circuit 216 and the low voltage output circuit 220.

In a typical operation the signal from the small electrodes 222, after being amplified by amplifier 224 will be monitored by the control unit 226. If that control unit senses only normal rhythm then nothing is done. If, however, the control unit were to sense a ventricular tachycardia then it would initiate antitachycardia pacing through the low voltage output circuit 220 and small electrodes 222. The formulas for calculating the timing of such ATP output pulse trains are well known in the art as listed in the background section. (An example is also discussed later in conjunction with FIG. 7.) The small electrodes, amplifier and control unit are also capable of diagnosing VF. If the antitachycardia pacing does accelerate the heart into a VF then this will be noted by the device. In that case the control unit 226 will immediately initiate the charging of capacitor 214 by charging circuit 212, the control unit 226 will also control the delivery of higher voltage pulses by means of output circuit 216 into the large cardiac electrodes 218. The application of these pulses with a typical amplitude of 30–200 V at a rate of 100–150 pulses per minute (typically) will be sufficient to generate repeated partial contractions of the heart. These partial contractions should be sufficient to maintain consciousness on the part of the patient. The patient can then call 911 or alert a bystander to provide transportation to a hospital. With the use of external defibrillation the patient should be restored to a normal rhythm at that point.

Figure 12:
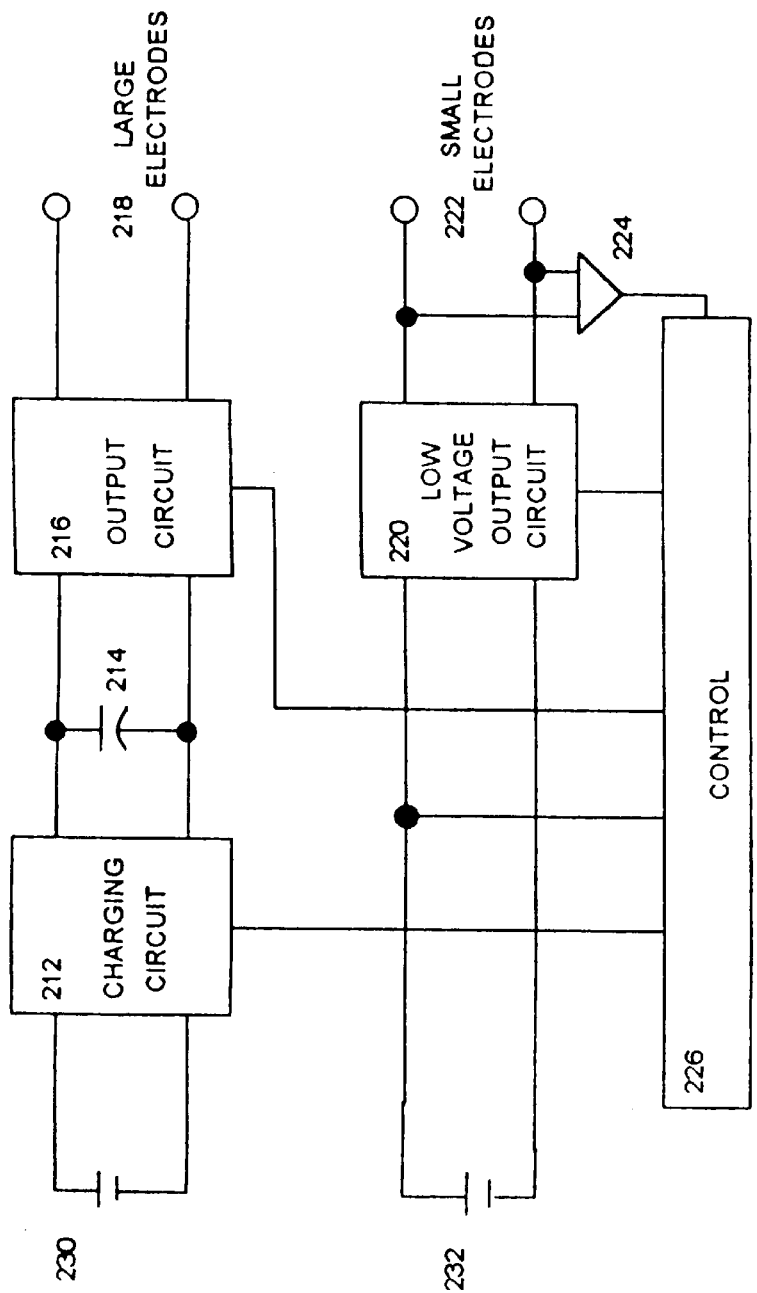
FIG. 12 shows an embodiment in which different batteries are used for the backup circuitry and the antitachycardia pacing circuitry.

FIG. 12 shows an embodiment which is identical except for the provision of two different battery energy sources. Battery 230 which provides power for the charging circuit 212 would have to be of a higher current output cell. The typical implantable battery chemistries which have appropriate performance are lithium silver vanadium oxide, titanium carbon monofluoride, or thionyl chloride. The battery 232 which provides the power for the low voltage output circuit 220 and the control unit 226 could be of a lower current output type such as a lithium iodine cell.

Figure 13:
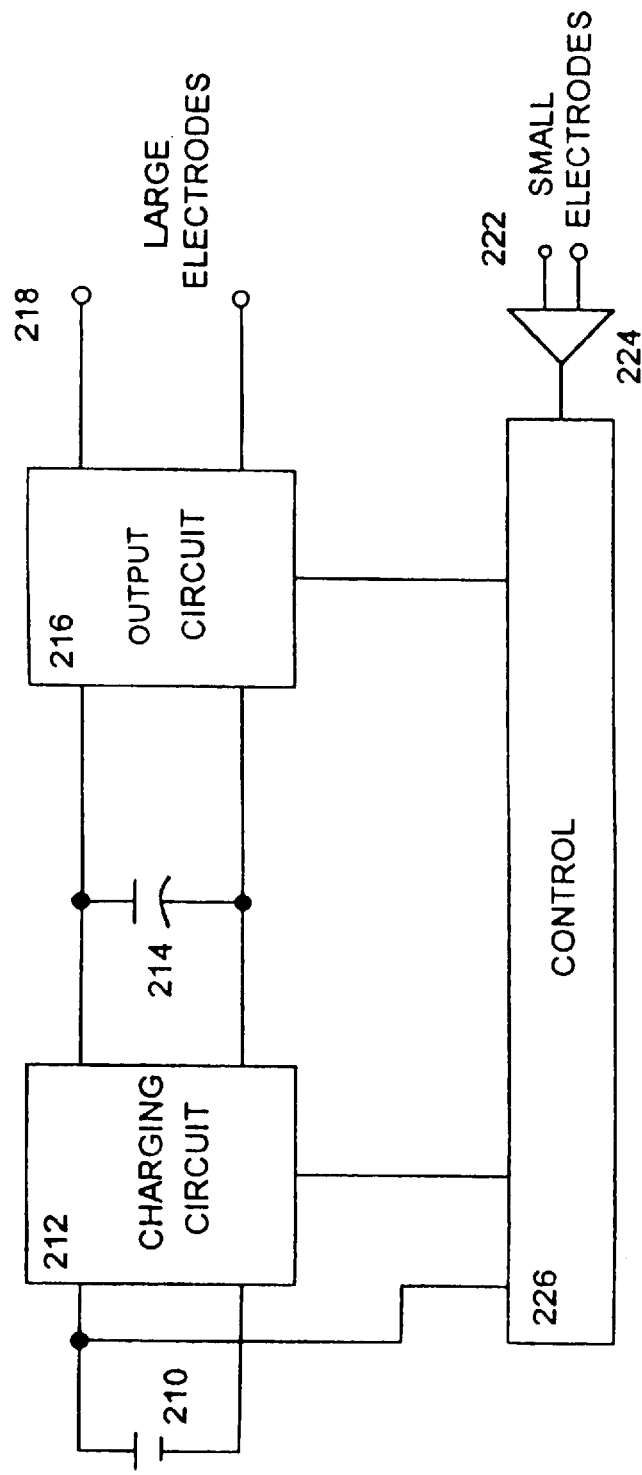
FIG. 13 shows an embodiment in which all pacing is done through the large electrodes.

FIG. 13 shows an alternative embodiment in which the antitachycardia pacing is done through the large electrodes 218 rather than through the small electrodes 222. With this approach the output circuit 216 is controlled to deliver voltages on the order of 5–30 volts for the initial antitachycardia pacing. In the event that this pacing was unsuccessful then higher voltage pulses could be used and delivered through the large electrodes 218. The use of large electrodes for antitachycardia pacing is taught in U.S. Pat. No. 5,330,509 of Kroll entitled "Far Field Antitachycardia Pacing." However, that invention did not anticipate the use of the electrical cardiac output forcing backup. In this embodiment of the instant invention, the small electrodes are still used for sensing the rhythm in order to make the correct diagnosis of VT or VF.

Figure 14:
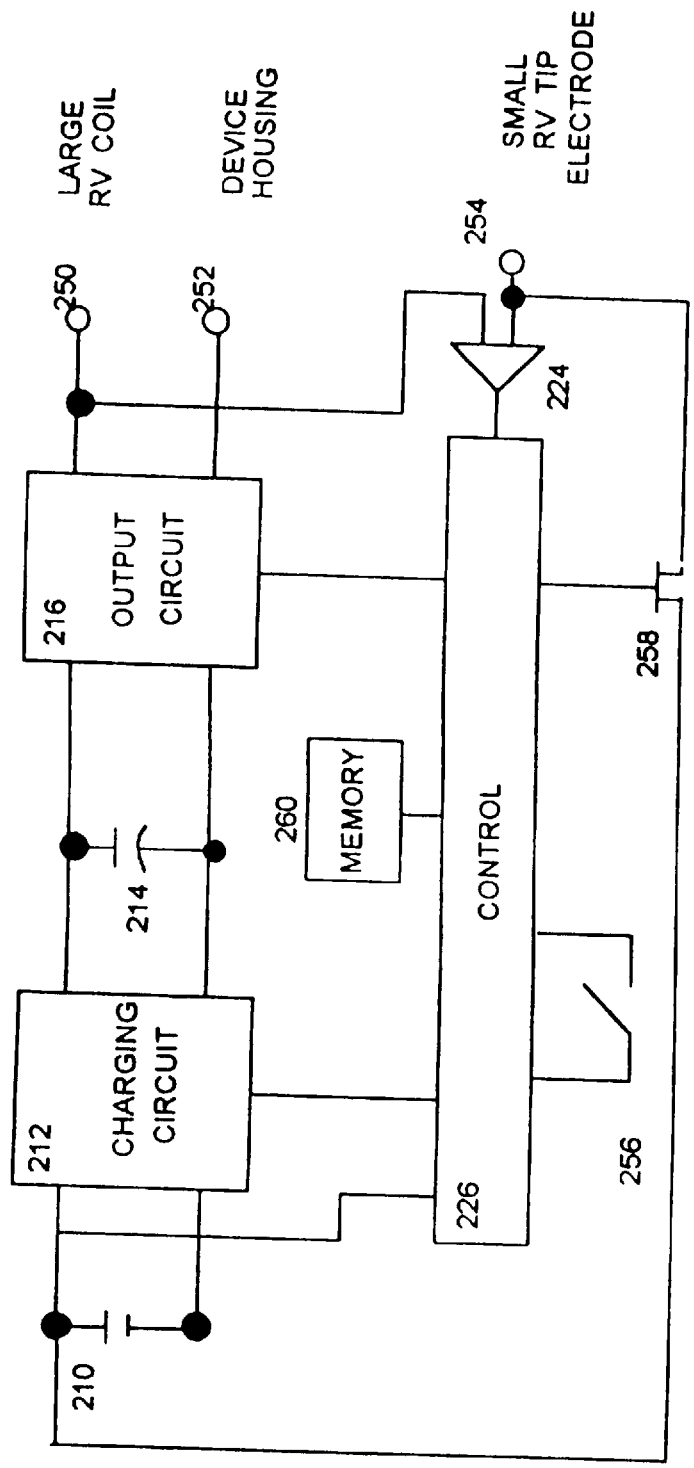
FIG. 14 shows a preferred embodiment in which a single small ventricular electrode is used.

FIG. 14 shows a preferred embodiment for the invention. The large electrodes are specifically a large right ventricular coil 250 with a longest linear dimension of at least one centimeter and preferably 2–8 centimeters. The other electrode for the ECOF backup is the device housing itself 252. A single small right ventricular tip electrode 254 is used for sensing with the large right ventricular coil 250 being the reference for the amplifier 224.

A magnetic reed switch 256 is monitored by the control unit and all output ceases with the application of a strong magnet over the patient's device. This could be used by the patient to stop the output but more likely by emergency personnel to turn the device off in order to more effectively perform external defibrillation.

Memory 260 is used to store programmable parameters, patient history, and patient stored electrograms.

Finally, the control unit uses transistor switch 258 to gate low voltage pacing pulses from the battery 210 to the small right ventricular tip electrode 254 for antitachycardia pacing. This could also be used for bradycardia pacing (therapy for patients with slow heart rates in the ventricle). It is common practice to use a negative voltage (cathodal) stimulation for such pacing. If desired, the conversion of the positive voltage from battery 210 to a negative pacing pulse is a trivial exercise for anyone skilled in the art.

Figure 15:
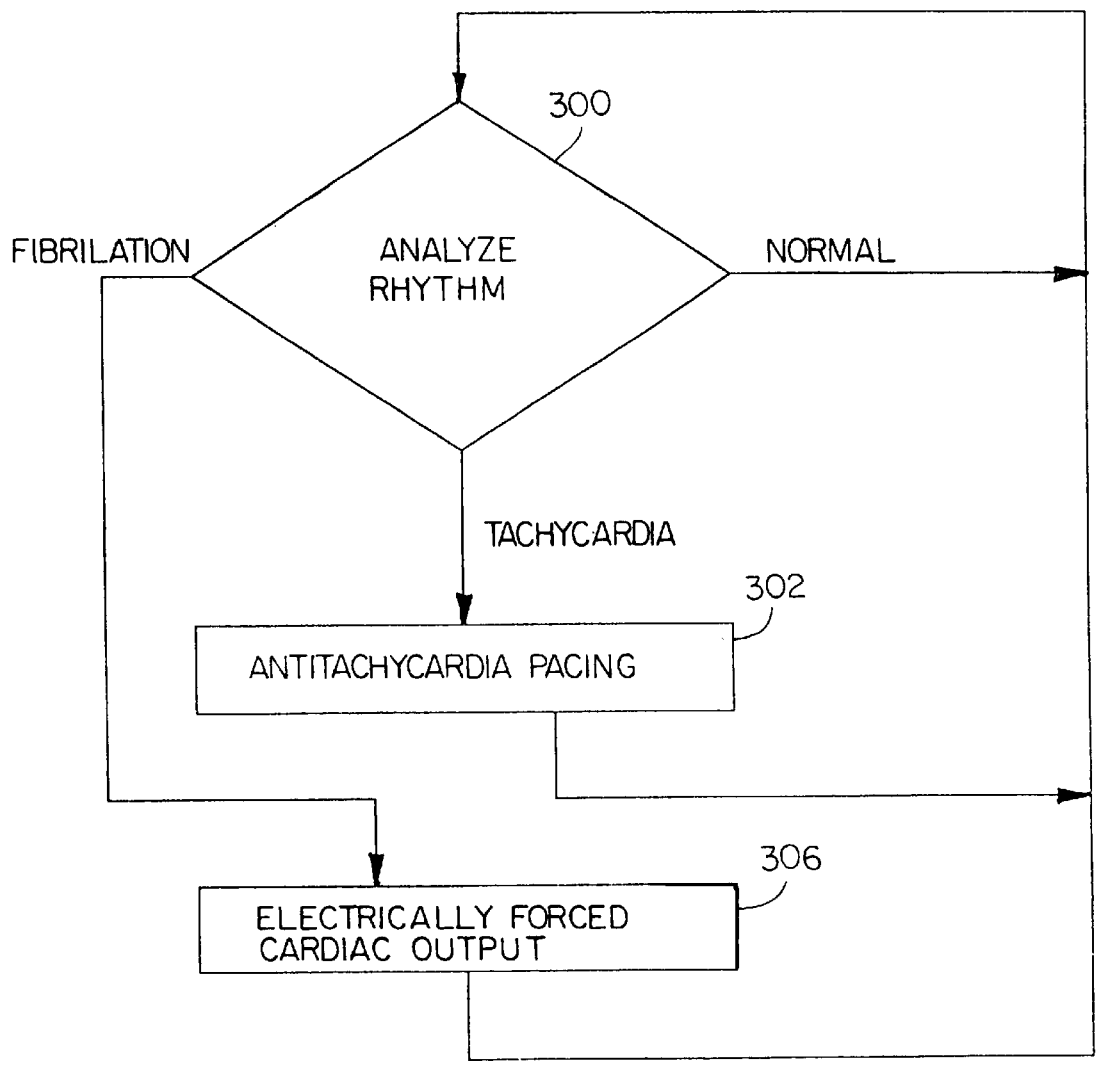
FIG. 15 shows the method of the invention.

FIG. 15 depicts the basic method of the invention. In step 300 the device senses and analyzes the rhythm. If a normal rhythm is sensed it simply stays in a waiting mode. If VT is sensed then the method proceeds to step 302 which is to perform antitachycardia pacing. After each attempt of antitachycardia pacing step 300 is used to analyze the rhythm. If the rhythm has returned to normal, then the method returns to monitoring. If VT is still sensed then the device again tries to perform ATP. If VF is sensed then the device proceeds to step 306 to force cardiac output electrically.

Figure 16:
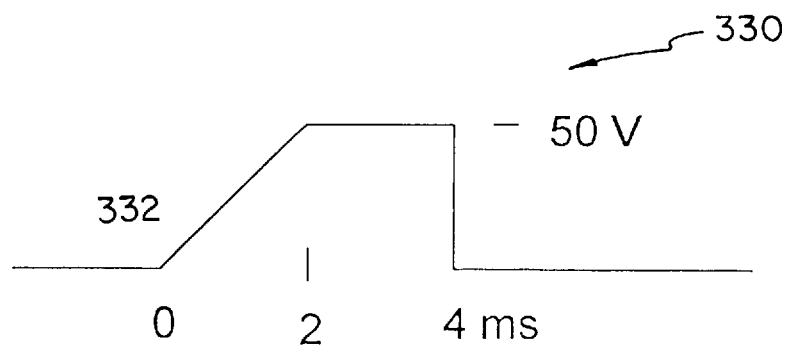
FIG. 16 depicts some possible cardiac output forcing pulses.
Figure 16:
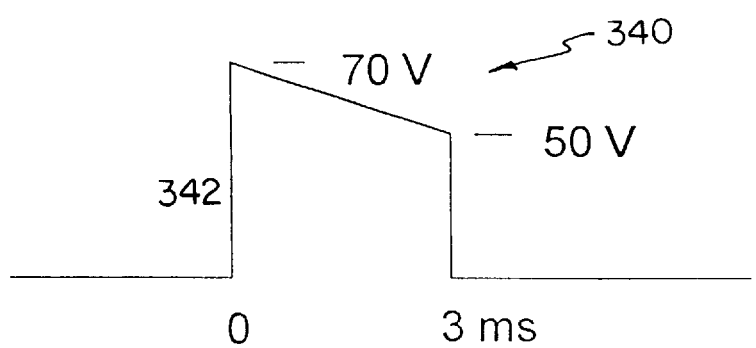

FIG. 16 depicts some of the pulses that are possible with such a device. Pulse 330 is a high comfort pulse. This pulse uses two milliseconds to climb from zero volts to full voltage. This full voltage is shown as 50 V in this example. The full voltage then is maintained for another 2 ms. This slow ramp 332 in the first 2 ms is less likely to stimulate nerve cells and skeletal muscles thus resulting in significantly less discomfort for the patient. However, this high comfort pulse is relatively inefficient as the output circuitry 216 (FIG. 14) must lose some energy (convert it to heat) by gradual turning on and thus is able to deliver fewer total pulses.

The high efficiency pulse 340 is generated by merely directly connecting the capacitor 214 (FIG. 14) through to the output electrodes 218 (FIG. 14) by means of a direct switch in the circuitry 216 (FIG.14). The voltage then follows the exponential decay of the capacitor which is shown here, as an example, decaying to 50 V over a period of 3 ms. Such a pulse is highly efficient in that essentially no energy is wasted in the output circuitry. However, the high frequency spectral content from the fast rising edge 342 can cause a great deal of patient discomfort.

Figure 17:
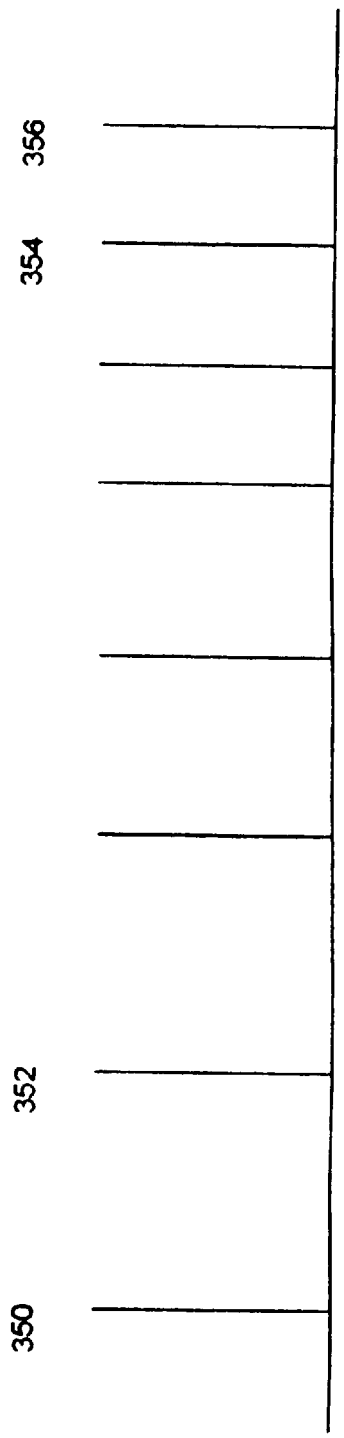
FIG. 17 shows a sample antitachycardia pacing burst.

FIG. 17 shows a typical antitachycardia pacing burst. The burst has 8 pulses in it. This type of burst is known as a "ramp" as the rate of the pulses increases during the burst. Note that the spacing between the first two pulses 350 and 352 is much greater than that between the last two pulses 354 and 356. A typical spacing for pulses between 350 and 352 is 95% of the spacing between cycles of the patient's ventricular tachycardia. However there are many other formulas for calculating these spacings and the size, number, and characteristics of such bursts which are very well covered in the literature and well known to those skilled in the art.

appropriate emergency authorities alerting them that the patient will need defibrillation within the next approximately 1 hour. The external receiver 408 could be made relatively sophisticated and could, for example, generate a detailed fax of the patient's condition which is then transmitted to the nearest emergency room. This fax could also include the various electrical signals recorded from inside the patient's heart. The use of fax transmission is taught in U.S. Pat. No. 5,336,245 of Adams et al. Alternatively, it could call a large battery of numbers such as the local emergency room, rescue squad, and patient's physician. It could also call relatives and neighbors who could be enlisted to provide transportation to the hospital.

The internal receiver 412 is used to convey programming parameters and operational commands from a physician.

There are many choices available for the battery. One choice would be the lithium silver vanadium oxide battery which is abbreviated SVO. This is the battery that is used in all present ICDs. It has the advantage of being able to deliver power at a very high rate. Its disadvantages are that its energy density is only about on the order of 1,000 joules per cubic centimeter (depending upon the construction) and that it is very expensive. The titanium carbon monofluoride battery has the advantage of an energy density on the order of 2,000 joules per cubic centimeter while the disadvantage is that it is only capable of delivery of about 1 watt of power while the SVO cell can deliver at a rate of at least 6 watts depending upon the construction.

The following table gives some examples of device lifetime and its dependence on the various factors of the output voltage, impedance, pulses per minute, and the battery capacity in joules. The voltage is practically limited to 375 V which the maximum rating for a modem photoflash capacitor.

| Voltage | Pulse width (ms) | Impedance | Energy/ Pulse | Pulses Per Min | Watts Ave | Battery Cap joules | Minutes Backup |
| --- | --- | --- | --- | --- | --- | --- | --- |
| 50 | 3 | 100 | 0.075 | 120 | 0.15 | 5000 | 556 |
| 100 | 3 | 100 | 0.3 | 120 | 0.6 | 5000 | 139 |
| 200 | 3 | 100 | 1.2 | 120 | 2.4 | 10000 | 69 |
| 30 | 3 | 100 | 0.027 | 150 | 0.0675 | 2000 | 494 |
| 70 | 3 | 100 | 0.147 | 150 | 0.3675 | 5000 | 227 |
| 100 | 3 | 100 | 0.3 | 120 | 0.6 | 5000 | 139 |
| 70 | 3 | 50 | 0.294 | 120 | 0.588 | 2000 | 57 |
| 70 | 3 | 50 | 0.294 | 60 | 0.294 | 2000 | 113 |

Figure 18:
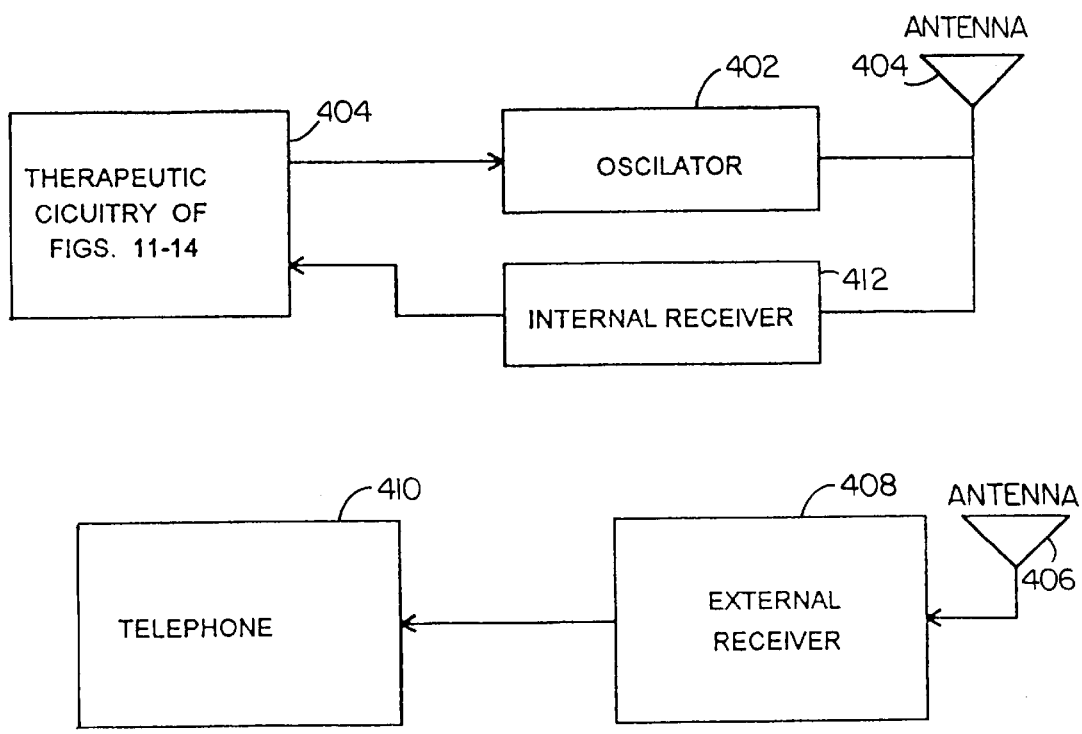
FIG. 18 shows a complete system.

FIG. 18 shows a complete system for the use of this device. The therapeutic circuitry shown in FIG. 11 through FIG. 14 is shown as system block 400. Added to this is an oscillator 402 which is used to transmit a signal through antenna 404. Antenna 404 could be a coil within the device, one of the defibrillation leads itself, or a separate antenna in the patient's body. That signal is then received by antenna 406 and processed by external receiver 408. That external receiver is then connected to a telephone 410.

In one embodiment the external receiver sits in the patient's place of living and is connected to the patient's home telephone. In another embodiment the external receiver is a small, very portable unit which is connected to a cellular phone. In operation, when the device 400 detects a VF, it then sends a signal through oscillator 402, antenna 404, antenna 406, and external receiver 408. The external receiver 408 generates a voice message which is channeled through telephone 410 to call a physician's office or the The calculations ignore converter inefficiencies, which will reduce backup time, yet do use conservative battery ratings, which will increase backup time. In all cases we assume a fixed pulse width of 3 milliseconds. In the first case ECOF pulses of 50 volts are used and the large electrode impedance is 100 ohms using an ECOF pulse rate of 120 pulses per minute and a battery capacity of 5,000 joules. The current would be 500 mA. There are 556 minutes of backup available, or in other words, nearly 10 hours. This is clearly excessive as the patient would find 10 hours of backup very uncomfortable and there are very few places in industrialized society in which the patient could not receive defibrillation within one hour. In the second case, we have a patient requiring a voltage of 100 volts to maintain adequate output. With everything else being the same, this reduces the minutes of backup to 139. It is conceivable that a patient could have a need for a relatively large voltage to maintain minimum cardiac output. An example given here is 200 volts. The current would increase to 2,000 mA. The battery capacity would have to be increased to 10,000 joules in order to maintain a 1 hour backup which is shown here as approximately 69 minutes.

Many patients should have sufficient cardiac output with 30 volt pulses. This would require a current of only 300 mA. If the rate of the ECOF pulses is increased to 150 pulses per minute to maximize output, then the battery capacity could be reduced down to 2,000 joules and the patient would still have 494 minutes of backup. If a patient needed a 70 volt pulse and a rate of 150 pulses per minute to maintain output and the earlier discussed battery capacity of 5,000 joules was used then there would be nearly 4 hours of backup available (actually 227 minutes). If this patient required 100 volt pulses and the pulsing rate was reduced to 120 pulses per minute, then the minutes of backup from the same battery would be reduced to 139, or a little over 2 hours.

In what should be the typical case, the patient will receive a 70 volt pulse at a rate of 120 pulses per minute with a small battery with only 2,000 joule capacity. This should give 57 minutes of backup. If the same patient were to have a rescue delayed then the pulse rate could be reduced to 60 per minute which would extend the minutes of backup to 113 or nearly 2 hours. As can be seen, there is a great deal of flexibility in the programming of the output voltage and the choice of battery capacity for different patients. A patient in an urban environment could get by with a very small battery while one that is in a rural environment might require a larger battery and an automatic telephoning system.

A 2,000 joule titanium carbon monofluoride battery should be on the order of 1 cubic centimeter in volume. If this battery were of the SVO type then its volume would be at least 2 cubic centimeters.

The capacitor could also be made very small. Assuming a 60 microfarad capacitance, even with the 200 volt maximum output shown in the table, the total stored energy would only be 1.2 joules. Modem electrolytic capacitors have an energy density of about 1 joules per cubic centimeter and thus this capacitor would have a volume of approximately 1 cm$^3$. Thus the total volume of the components for the energy (namely the battery and capacitor) would have volumes on the order of 2 or 3 cm$^3$ compared to volumes of 20–30 cm$^3$ or more in the present ICDs.

It should be understood that various alternatives to the embodiments of the invention described herein may be employed in practicing the invention. For example, while most of the discussion is in the context of an implantable device, the concepts of the invention are also applicable to external delivery systems. It is intended that the following claims define the scope of the invention and that structures and methods within the scope of these claims and their equivalents be covered thereby.

That which is claimed is:

1. An implantable device for treating ventricular tachycardia with electrical pacing therapy consisting of:
    a. at least one battery;
    b. a pacing pulse generating circuit connected to said battery;
    c. at least one small electrode for placement in a patient's heart connected to the pacing pulse generator circuitry;
    d. a control circuit connected to the pacing pulse generating circuit to generate pulses of appropriate timing to abolish the ventricular tachycardia according to the techniques of antitachycardia pacing;
    e. a charging circuit connected to at least one battery capable of charging a capacitor to a voltage of 30–350 volts at least once per second;
    f. a capacitor for storing energy from the charging circuit;
    g. at least one large electrode for placement in a patient's heart; and
    h. an output circuit for delivering pulses from the capacitor to said at least one large electrode, so that, in the event that the antitachycardia pacing causes the ventricular tachycardia to transform into a lethal ventricular fibrillation, the large electrode pulses will electrically force cardiac output to maintain life until the patient could be externally defibrillated.

2. The apparatus of claim 1 in which the large electrode has a greatest dimension of greater than one centimeter.

3. The device of claim 1 in which the control circuit cooperates with the output circuit to restrict the rise time of at least one gradual edge to greater than 100 microseconds.

4. The device of claim 1 in which the control circuit cycles the output circuit so that the output waveform has at least 6 narrow pulses in it.

5. The device of claim 1 in which the pacing pulse generating circuit battery is distinct from the charging circuit battery.

6. The device of claim 1 in which the pacing electrode is actually the same as the large electrode.

7. The device of claim 1 in which the control circuit cycles the output circuit so that the high voltage pulses are delivered at a rate of 60–200 pulses per minute.

8. A method for electrically terminating a ventricular tachycardia in a patient, comprising the steps of:
    a. providing a plurality of electrodes in the patient's chest;
    b. detecting the presence of a tachycardia in the patient via said electrodes;
    c. delivering electrical current pulses of a low voltage to the patient's heart via some of said electrodes after detecting the tachycardia;
    d. monitoring for possible ventricular fibrillation;
    e. in the event of the detection of ventricular fibrillation delivering higher voltage electrical pulses to the patient's heart via some of said electrodes at a rate between 60 and 200 pulses per minute, to directly force contraction in the patient's heart whereby a minimum level of cardiac output sufficient to maintain life is provided by said electrical current pulses.

9. The method of claim 8 further comprising the step of slowing the rise time of the higher voltage pulse to give the higher voltage pulse a rise time greater than 100 microseconds thereby minimizing patient discomfort and chest twitching.

10. The method of claim 8 further comprising the step of forming each higher voltage pulse of a train of at least 10 narrow pulses thereby minimizing patient discomfort and chest twitching.

11. The method of claim 8 further comprising the step of controlling the output voltage so that the higher voltage pulses have an amplitude of 30–350 volts.

12. The method of claim 8 further comprising the step of providing a high current output circuit so that the higher voltage pulses have a current of greater than 300 milliamperes.

13. The method of claim 8 in which at least one of the electrodes has a dimension greater than 1 cm.

14. The method of claim 8 in which the low voltage pulses of part c are delivered via the same electrodes as used for the higher voltage pulses of part e.

15. The method of claim 8 comprising the additional step of automatically communicating with another party in the event of ventricular fibrillation.

16. A device, for implantation in the human body, for performing antitachycardia pacing, and for maintaining cardiac output of a patient's heart during a possible ventricular fibrillation induced by said antitachycardia pacing using electrical forcing fields comprising:

a. means for supplying battery power;
   b. an arrhythmia detector connected to said means for supplying batter power;
   c. a communication connection from said means for supplying battery power and said arrhythmia detector to the patient's heart; and
   d. an output control circuit connected to said arrhythmia detector and to said means for supplying battery power and communicatively adapted to be connected to the heart for delivering multiple electrical current pulses to the heart after detection of a fibrillation, said electrical current pulses having a voltage between 30–350 volts and current greater than 300 mA whereby contraction of the patient's heart is directly forced by said current pulses to generate a minimum level of cardiac output sufficient to maintain life.

17. The device of claim 16 further comprising bradycardia output pacing means.

18. The device of claim 16 in which the output control means includes an inverter powered by said battery and driving a high energy capacitor.

19. The device of claim 16 further comprising means to automatically alert another party in the event of ventricular fibrillation.

20. The device of claim 16 further comprising means for storing programmable parameters for the detection of the arrhythmias, the antitachycardia pacing parameters, and the electrical cardiac output forcing parameters.

21. The device of claim 16 further comprising means to store the patient's internal electrical signals.

22. The device of claim 16 further comprising blood pressure monitoring means connected to said arrhythmia detection means.

23. The device of claim 22, in which said blood pressure monitoring means monitors cardiac output and further comprising the step of adjusting said electrical current pulse amplitude by said output control means to maintain predetermined level of cardiac output based on blood pressure thereby conserving battery means.

* * * * *